US012618774B2

(12) United States Patent (10) Patent No.: US 12,618,774 B2

Schonbrun et al. (45) Date of Patent: May 5, 2026

(54) FLUID TESTING SYSTEM

(71) Applicant: Instrumentation Laboratory Co., Bedford, MA (US)

(72) Inventors: Ethan F. Schonbrun, Auburndale, MA (US); Christopher Farren, Bedford, MA (US); Paul C. McCormack, Carlisle, MA (US); Luisa Andruzzi, Bedford, MA (US)

(73) Assignee: Instrumentation Laboratory Co., Bedford, MA (US)

( * ) Notice: Subject to any disclaimer, the term of this patent is extended or adjusted under 35 U.S.C. 154(b) by 0 days.

(21) Appl. No.: 17/722,049

(22) Filed: Apr. 15, 2022

(65) Prior Publication Data

US 2023/0333013 A1 Oct. 19, 2023

(51) Int. Cl.
  *G01N 21/00* (2006.01)
  *G01N 21/51* (2006.01)
  (Continued)

(52) U.S. Cl.
  CPC ........... *G01N 21/51* (2013.01); *G01N 33/487* (2013.01); *G01N 21/00* (2013.01); *G01N 21/03* (2013.01);
  (Continued)

(58) Field of Classification Search
  CPC ...... G01N 21/51; G01N 33/487; G01N 21/00; G01N 21/47; G01N 33/48; G01N 33/483;
  (Continued)

(56) References Cited

U.S. PATENT DOCUMENTS 3,951,608 A    4/1976   Trod
4,229,104 A    10/1980  Lahme et al.
        (Continued)

FOREIGN PATENT DOCUMENTS

CN        202092944 U    12/2011
EP        1181098 A1     2/2002
        (Continued)

OTHER PUBLICATIONS

Fulghum, Lisa ("Z-Dimensions Are Not Created Equal", Apr. 30, 2013, World Precision Instruments, https://www.wpiinc.com/blog/category/spectroscopy) (Year: 2013).*

(Continued)

*Primary Examiner* — Michelle M Iacoletti
*Assistant Examiner* — Judy Dao Tran
(74) *Attorney, Agent, or Firm* — ArentFox Schiff LLP

(57) ABSTRACT

Technology described herein includes a method that includes providing, by an optical light source, a light beam configured to traverse an optical path through a fluid comprising the biological sample in a container. A length of the optical path through the fluid is between 3.3 mm to 5.5 mm, and a center of the light beam is at a height less than 1.6 mm from a bottom interior surface of the container, and a volume of the fluid is less than 120 µL. An optical detector receives optical information after the light beam traverses the optical path. An output of the optical detector is associated with at least one parameter representing the one or more characteristics of the biological sample.

8 Claims, 5 Drawing Sheets

(51) Int. Cl.

| | |
|---|---|
| *G01N 33/487* | (2006.01) |
| *G01N 21/03* | (2006.01) |
| *G01N 21/47* | (2006.01) |
| *G01N 33/48* | (2006.01) |
| *G01N 33/483* | (2006.01) |
| *G01N 33/72* | (2006.01) |
| *G01N 35/10* | (2006.01) |

(52) U.S. Cl.
CPC ..... *G01N 2021/0382* (2013.01); *G01N 21/47* (2013.01); *G01N 2021/513* (2013.01); *G01N 33/48* (2013.01); *G01N 33/483* (2013.01); *G01N 33/72* (2013.01); *G01N 35/1009* (2013.01); *G01N 2201/1235* (2013.01)

(58) Field of Classification Search
CPC .............. G01N 33/72; G01N 35/1009; G01N 2201/1235
See application file for complete search history.

(56) References Cited

U.S. PATENT DOCUMENTS

| | | | |
|---|---|---|---|
| 4,787,744 A | 11/1988 | Hissung | |
| 5,098,661 A | 3/1992 | Froehlich et al. | |
| D330,428 S | 10/1992 | Lewis et al. | |
| 5,258,620 A * | 11/1993 | Sueyasu | G01N 33/04 |
| | | | 250/343 |
| D380,555 S | 7/1997 | Kurosaki et al. | |
| 6,249,345 B1 | 6/2001 | Kraack | |
| 6,403,037 B1 | 6/2002 | Chang et al. | |
| 6,881,541 B2 | 4/2005 | Petersen et al. | |
| 6,887,432 B2 | 5/2005 | Kansy et al. | |
| 7,105,093 B2 | 9/2006 | de Gheldere et al. | |
| 7,138,091 B2 | 11/2006 | Lee et al. | |
| D560,816 S | 1/2008 | Talmer et al. | |
| 7,611,672 B1 | 11/2009 | Fukunaga et al. | |
| D621,520 S | 8/2010 | Talmer et al. | |
| 7,927,876 B2 | 4/2011 | Blouin et al. | |
| D661,403 S | 6/2012 | Connelly et al. | |
| 8,211,386 B2 | 7/2012 | Talmer et al. | |
| 8,313,713 B2 | 11/2012 | Jacobs et al. | |
| 8,323,585 B2 * | 12/2012 | Heavner | B01L 3/5021 |
| | | | 222/251 |
| 8,448,800 B2 | 5/2013 | Konrad | |
| 8,493,559 B2 | 7/2013 | Harvard | |
| D687,566 S | 8/2013 | Trump | |
| D687,964 S | 8/2013 | Trump | |
| 8,518,347 B2 | 8/2013 | Tajima | |
| 8,591,836 B2 | 11/2013 | Boege et al. | |
| 8,605,279 B2 | 12/2013 | Gotschy et al. | |
| 8,714,800 B2 | 5/2014 | Kobayashi et al. | |
| 8,808,649 B2 | 8/2014 | Ingber et al. | |
| 8,840,837 B2 | 9/2014 | Smith et al. | |
| 9,005,543 B2 | 4/2015 | Grenz et al. | |
| 9,017,536 B2 | 4/2015 | Oishi et al. | |
| D743,045 S | 11/2015 | Trump | |
| 9,360,422 B2 | 6/2016 | Koerperick et al. | |
| 9,463,458 B2 | 10/2016 | Valla | |
| 9,464,981 B2 | 10/2016 | Gibbons | |
| 9,540,675 B2 | 1/2017 | De Forest et al. | |
| 9,707,528 B2 | 7/2017 | Suchocki et al. | |
| 9,739,704 B2 | 8/2017 | Voit et al. | |
| D808,036 S | 1/2018 | Langhoff et al. | |
| 10,092,697 B2 | 10/2018 | Nessel et al. | |
| 10,137,447 B1 | 11/2018 | Motadel et al. | |
| D839,448 S | 1/2019 | Langhoff et al. | |
| 10,220,383 B2 | 3/2019 | Laukkonen et al. | |
| 10,300,482 B2 | 5/2019 | Cooney et al. | |
| 10,371,604 B2 | 8/2019 | Rath et al. | |
| 10,376,878 B2 | 8/2019 | Calanca et al. | |
| 10,391,497 B1 | 8/2019 | Gong et al. | |
| 10,989,724 B1 * | 4/2021 | Holmes | G01N 35/02 |
| 11,262,371 B2 | 3/2022 | Fukaya et al. | |
| D953,569 S | 5/2022 | Matsuoka et al. | |

| | | | |
|---|---|---|---|
| 2002/0155035 A1 | 10/2002 | Kansy et al. | |
| 2005/0013746 A1 | 1/2005 | Lee et al. | |
| 2005/0042145 A1 | 2/2005 | Ueda et al. | |
| 2005/0271550 A1 | 12/2005 | Talmer et al. | |
| 2007/0019189 A1 | 1/2007 | Marsteller et al. | |
| 2007/0081159 A1 * | 4/2007 | Giffin | G01N 21/03 |
| | | | 356/440 |
| 2007/0140919 A1 | 6/2007 | Clarkson et al. | |
| 2008/0026476 A1 | 1/2008 | Howell et al. | |
| 2008/0260585 A1 | 10/2008 | Murakami | |
| 2009/0117005 A1 | 5/2009 | Rousseau | |
| 2011/0107855 A1 | 5/2011 | Motadel | |
| 2011/0306087 A1 * | 12/2011 | Galiano | G01N 21/51 |
| | | | 435/288.7 |
| 2011/0308335 A1 | 12/2011 | Pink et al. | |
| 2012/0189510 A1 | 7/2012 | Kim et al. | |
| 2015/0231630 A1 | 8/2015 | Chow et al. | |
| 2017/0030827 A1 | 2/2017 | Nickel et al. | |
| 2017/0307525 A1 * | 10/2017 | Langhoff | G01N 21/51 |
| 2018/0169648 A1 | 6/2018 | Trau et al. | |
| 2018/0353957 A1 | 12/2018 | Bishop et al. | |
| 2018/0369806 A1 * | 12/2018 | Behnk | B01L 3/508 |
| 2019/0002956 A1 | 1/2019 | Stumbo et al. | |
| 2020/0057880 A1 | 2/2020 | Mizutani et al. | |
| 2020/0264207 A1 * | 8/2020 | Kubota | G01N 35/1016 |
| 2020/0324282 A1 | 10/2020 | Postier et al. | |
| 2021/0318348 A1 | 10/2021 | Holmes et al. | |
| 2022/0003685 A1 * | 1/2022 | Ando | G01N 21/0303 |
| 2024/0044918 A1 * | 2/2024 | Taagaard | G01N 33/492 |

FOREIGN PATENT DOCUMENTS

| | | | | | |
|---|---|---|---|---|---|
| EP | 1702210 | A2 | 9/2006 | | |
| EP | 2450690 | A1 | 5/2012 | | |
| EP | 2466291 | A1 | 6/2012 | | |
| EP | 2492015 | A1 | 8/2012 | | |
| EP | 2514528 | A1 | 10/2012 | | |
| EP | 2968059 | B1 | 2/2018 | | |
| EP | 3548181 | A1 | 10/2019 | | |
| EP | 3938287 | A1 | 1/2022 | | |
| JP | H1114632 | A * | 1/1999 | | G01F 23/28 |
| JP | 2007-139767 | A | 6/2007 | | |
| JP | 4950947 | B2 | 6/2012 | | |
| JP | 5086286 | B2 | 11/2012 | | |
| JP | 2012-242231 | A | 12/2012 | | |
| JP | 2016-217921 | A | 12/2012 | | |
| JP | 2019500585 | A * | 1/2019 | | G06V 10/50 |
| JP | 2020-091185 | A | 6/2020 | | |
| WO | WO2002040131 | A1 | 5/2002 | | |
| WO | WO 2010039975 | A1 | 4/2010 | | |
| WO | WO2011135115 | A1 | 11/2011 | | |
| WO | WO2022031459 | A1 | 2/2022 | | |

OTHER PUBLICATIONS

Extended European Search Report in European Appln. No. 23162781.1, dated Jun. 5, 2023, 6 pages.
Search Report and Written Opinion in Luxembourg Appln. No. LU102965, dated Dec. 14, 2022, 11 pages.
Office Action in Japanese Appln. No. 2023-016727, mailed on Oct. 17, 2023, 9 pages (with English Translation).
Office Action issue in Australian Appln. No. 2023201898, dated Jan. 23, 2024, 3 pages.
Extended European Search Report in European Appln. No. 23170530.2, dated Aug. 1, 2023, 10 pages.
Shop.brand.de [online], "Cuvettes, macro and semi-micro, PS, Certified Life Science Quality," published date unknown, retrieved on Aug. 25, 2023, retrieved from URL<https://shop.brand.de/en/cuvettes-macro-and-semi-micro-ps-certified-life-science-guality-p7192.html>, 1 page.
Office Action in Australian Appln. No. 2023201898, dated Mar. 25, 2024, 3 pages.
wilsonanalytical.com [online], "Cuvettes Guide," available on or before Feb. 26, 2024, via Internet Archive: Wayback Machine URL <https://web.archive.org/web/20240226002517/https://wilsonanalytical.com/pages/cuvettes-guide>, retrieved on May 30, 2024, URL<https://wilsonanalytical.com/pages/cuvettes-guide>, 4 pages.

(56)     References Cited

OTHER PUBLICATIONS

Notice of Acceptance in Australian Appln. No. 2023201898, mailed on Dec. 18, 2024, 3 pages.
Office Action in Australian Appln. No. 2023201898, mailed on Dec. 10, 2024, 3 pages.
Office Action in Australian Appln. No. 2023201898, dated Aug. 20, 2024, 3 pages.
European Search Report received for European Patent Application No. 23170530, Jul. 21, 2023, 2 pages.
Office Action received for European Patent Application No. 23170530.2, Mar. 3, 2025, 5 pages.
European Search Report received for European Patent Application No. 23162781, May 20, 2023, 2 pages.
Office Action received for Chinese Patent Application No. 202310343743.8, Feb. 12, 2026, 22 pages. (English and Chinese versions).

* cited by examiner

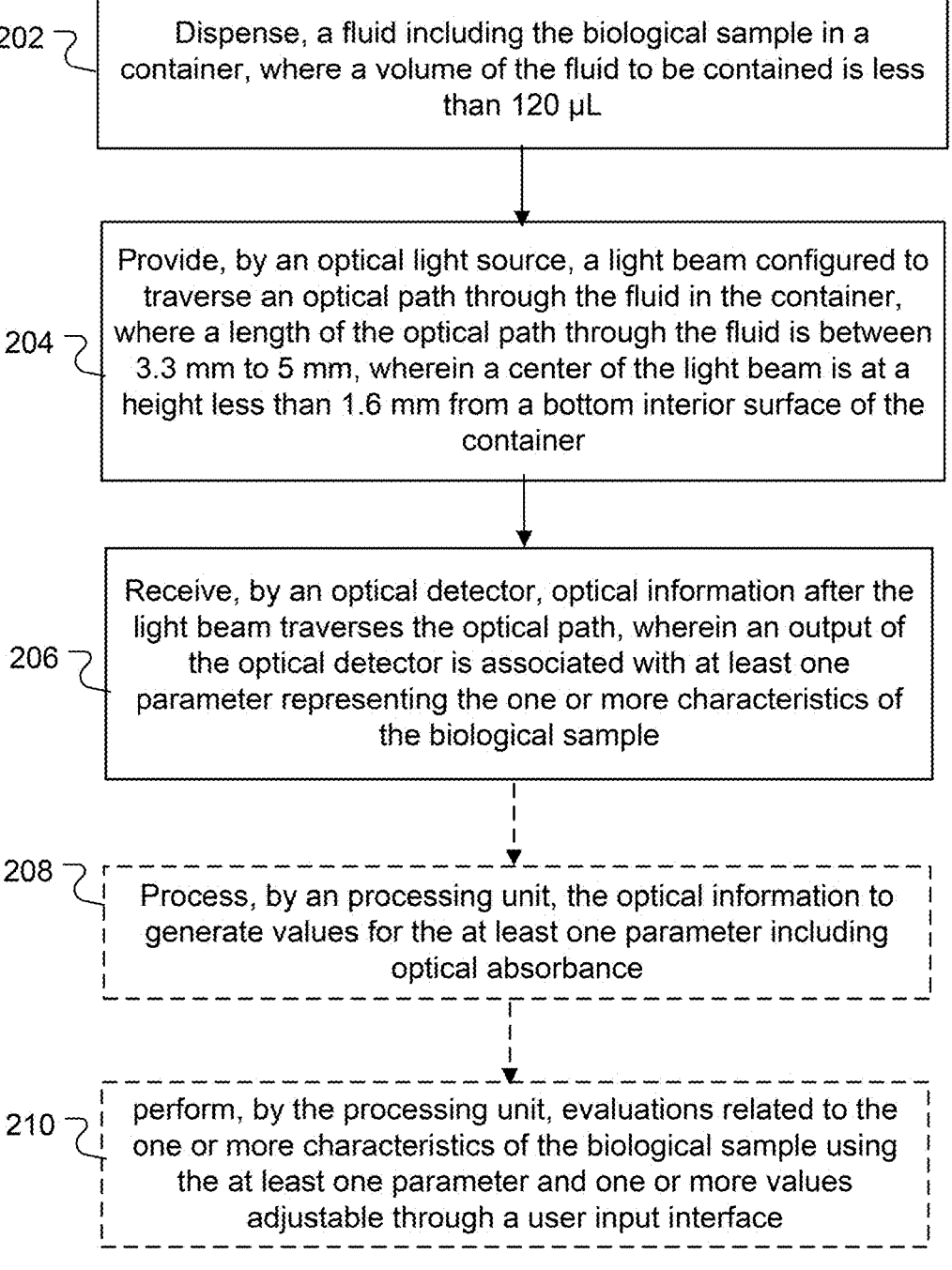

202 — Dispense, a fluid including the biological sample in a container, where a volume of the fluid to be contained is less than 120 µL 204 — Provide, by an optical light source, a light beam configured to traverse an optical path through the fluid in the container, where a length of the optical path through the fluid is between 3.3 mm to 5 mm, wherein a center of the light beam is at a height less than 1.6 mm from a bottom interior surface of the container 206 — Receive, by an optical detector, optical information after the light beam traverses the optical path, wherein an output of the optical detector is associated with at least one parameter representing the one or more characteristics of the biological sample 208 — Process, by an processing unit, the optical information to generate values for the at least one parameter including optical absorbance 210 — perform, by the processing unit, evaluations related to the one or more characteristics of the biological sample using the at least one parameter and one or more values adjustable through a user input interface

FLUID TESTING SYSTEM

TECHNICAL FIELD

This specification generally relates to fluid testing devices and systems.

BACKGROUND

A fluid testing device or system performs analysis of the properties of a biological sample, such as blood or another body fluid. An example of fluid testing is hemostasis testing used in diagnosis of various hemostatic disorders. In some fluid testing systems, a biological sample is dispensed into a container (e.g., a cuvette) and mixed with one or more reagents. The system can include an optical interrogation system that generates a light beam configured to traverse an optical path through the fluid in the container and measures one or properties of the light beam thereafter. Various properties of the fluid in the container can be determined/ identified based on information derived from the measured properties of the light beam.

SUMMARY

In one aspect, this document describes a system for determining one or more characteristics of a biological sample. The system includes a container configured to contain a fluid including the biological sample, where a volume of the fluid to be contained is less than 120 μL; an optical source providing a light beam configured to traverse an optical path through the fluid in the container, where a length of the optical path through the fluid is less than 6 mm, the optical source being positioned relative to the container such that a center of the light beam is at a height less than 1.6 mm from a bottom interior surface of the container; and an optical detector configured to receive optical information after the light beam traverses the optical path, wherein an output of the optical detector is associated with at least one parameter representing the one or more characteristics of the biological sample.

In another aspect, this document describes a container that includes a lower portion enclosed by (i) a first pair of surfaces that are substantially parallel to each other, a separation between the first pair of surfaces being in a range 3.3 mm to 6 mm, and (ii) a second pair of surfaces that are substantially parallel to each other and substantially perpendicular to the first pair of surfaces, a separation between the second pair of surfaces being less than 6 mm; and an upper portion connected to the lower portion, the upper portion enclosed by at least a third pair of surfaces that are divergent with respect to each other, wherein the lower portion is configured to contain a fluid including a biological sample, wherein a height of the lower portion is such that the lower portion is configured to hold a volume of the fluid no more than 120 μL.

In another aspect, this document describes a method for determining one or more characteristics of a biological sample. The method includes providing, by an optical light source, a light beam configured to traverse an optical path through a fluid including the biological sample in a container, where a length of the optical path through the fluid is between 3.3 mm to 5.5 mm, wherein a center of the light beam is at a height less than 1.6 mm from a bottom interior surface of the container, where a volume of the fluid is less than 120 μL; and receiving, by an optical detector, optical information after the light beam traverses the optical path, wherein an output of the optical detector is associated with at least one parameter representing the one or more characteristics of the biological sample.

Implementations of the above aspects can include one or more of the following features. The method can further include aspirating, by a probe, a portion of the fluid in the container, wherein a volume of the fluid remaining in the container after aspiration is less than 35% of the volume of the fluid in the container before the aspiration; and dispensing, by the probe, the aspirated portion of the fluid back into the container. The volume of the fluid remaining in the container after the aspiration is adjustable through a user input interface. The volume of the fluid to be contained is less than 100 μL, less than 75 μL, or less than 50 μL. The length of the optical path through the fluid is 4 mm. Length and width of a portion of the container configured to contain the fluid is between 3.3 mm to 5.5 mm and between 3.3 mm to 5.5 mm, respectively. The method can further include receiving, by a processing unit, the optical information; processing, by the processing unit, the optical information to generate values for the at least one parameter including optical absorbance; and performing, by the processing unit, evaluations related to the one or more characteristics of the biological sample using the at least one parameter and one or more values adjustable through a user input interface. The method can further include receiving, by a processing unit, information indicative of a composition of the fluid in the container; and determining, by the processing unit, based on the information indicative of the composition of the fluid, a dispense height of a corresponding probe above a surface of the fluid for dispensing at least one of the biological sample or a reagent component of the fluid, wherein the determining of the dispense height of the corresponding probe accounts for surface tension interactions between the fluid and walls of the container. The dispense height is between 2 mm and 4 mm from an average liquid level of the fluid in the container.

Particular implementations of the subject matter described in this disclosure can be implemented to realize one or more of the following advantages. Fluid testing can be performed using a container that is configured to contain a relatively small amount of fluid or assay (e.g., less than 120 μL). The reduction in optical path through the fluid in such small containers—which may otherwise affect the accuracy of measurements—can be offset by efficient mixing of samples and reagents within the small volume of the container, thereby reducing fluidic noise in the assay. The reduced dimensions of the container (as compared to e.g., existing containers that may require 150 μL or more of reaction volume for proper testing) facilitates usage of smaller volumes of patient samples (e.g., whole blood or plasma) and/or reagents. In some cases, this can allow for more tests to be performed with an available amount of reagent, thereby potentially reducing disposal requirements of the reagent packaging. Because the container requires less sample volume or reaction volume per test, the implementations of the present disclosure can improve the efficiency of the fluid testing process, for example, by reducing the time needed to aspirate and dispense samples and reagents into the container.

The effects of a shorter optical path length (e.g., reduced absorbance) can be substantially offset by an improved mixing process that reduces fluidic noise, therefore potentially leaving the overall signal to noise ratio (SNR) of the fluid testing approximately unchanged (or even improved) as compared to the SNR associated with some existing containers. The improved mixing process may be realized, for example, via an aspirate-dispense mixing process that uses a low blind volume (i.e., volume of the fluid remaining in the container after aspiration). Such low blind volumes (e.g., 65 µL or less, or 35% or less of the original total volume)—that are facilitated by the reduced dimensions of the container—can in some cases help improve the mixing efficacy of the sample and the reagent. This in turn can potentially reduce the fluidic noise and improve the quality and sensitivity of the fluid testing result. Parameters of the fluid testing system can be adapted with the reduced size (e.g., length) of the container, and the parameters can be adjusted through a user input interface.

In some cases, certain implementations of the present disclosure (e.g., a container with 3.3 mm to 5.5 mm optical path length) can have higher interference tolerance (e.g., to hemolysis, bilirubin and lipemia) as compared to that associated with a container with longer optical path length (e.g., 6 mm to 7 mm) due to the larger dynamic range of the measurable concentration. Therefore, the implementations of the present disclosure can have potentially higher tolerance to pre-analytical issues such as determining hemolysis, bilirubin, or lipemia.

It is appreciated that methods and systems in accordance with the present disclosure can include any combination of the aspects and features described herein. That is, methods and systems in accordance with the present disclosure are not limited to the combinations of aspects and features specifically described herein, but also may include any combination of the aspects and features provided.

The details of one or more implementations of the present disclosure are set forth in the accompanying drawings and the description below. Other features and advantages of the present disclosure will be apparent from the description and drawings, and from the claims.

BRIEF DESCRIPTION OF DRAWINGS

FIG. 2 is a flowchart of an example process for performing fluid testing in accordance with technology described herein.

Like reference numbers and designations in the various drawings indicate like elements.

DETAILED DESCRIPTION

Figure 1:
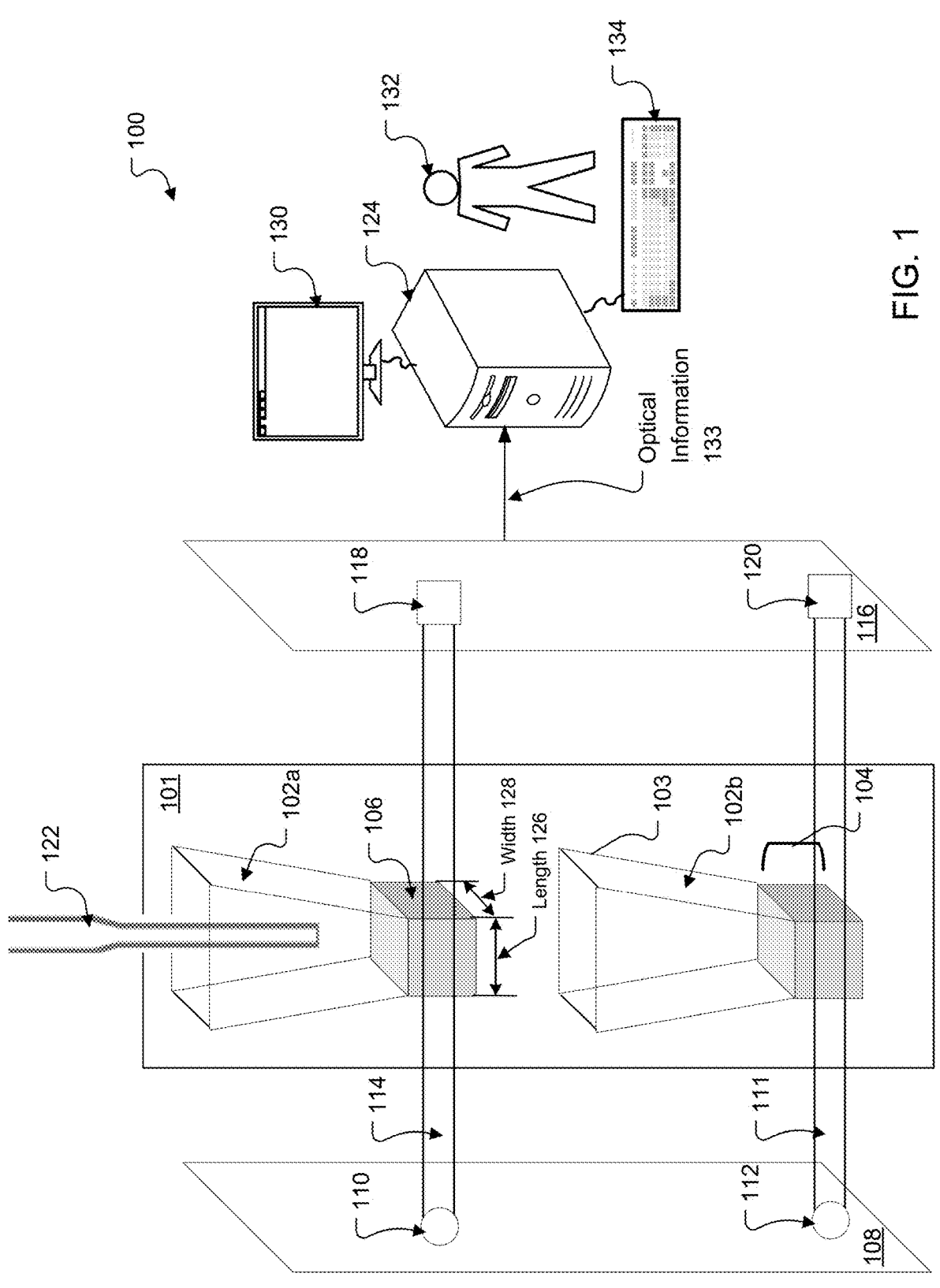
FIG. 1 is a diagram of an example system configured to implement technology described herein.

In typical fluid testing systems that rely on optical interrogation, the optical path length (the distance that an optical beam traverses through a fluid being tested) is usually maintained above a threshold distance. This is because a threshold absorbance of light by the fluid may be needed for accurate determination of certain parameters or characteristics associated with the fluid. Absorbance A is proportional to the path length L under Beer-Lambert law, i.e., $A=\varepsilon Lc$, wherein $\varepsilon$ is the molar attenuation coefficient of the attenuating species and c is the concentration of the attenuating species. Dimensions of a container that holds the fluid during the optical interrogation are configured to provide such threshold path length. For example, certain existing containers (e.g., the containers currently used in the ACL Top family of hemostasis testing systems developed by Werfen—referred herein as the "ACL TOP cuvette", the containers used in the systems or platforms developed by Siemens, such as Siemens-Sysmex CS-2500 and CS-5100, and the containers used in the systems or platforms developed by Roche, such as Roche cobas t 511) are configured to provide at least 4.9 mm, 5mm, 6 mm, or more of optical path length. Such containers can in turn require a threshold reaction volume of fluid (e.g., 150 µL fluid that includes at least 50 µL sample of blood plasma) for accurate measurements.

The fluid in the container typically is a mixture of reagent(s) and a sample. The disclosed systems/methods herein are not limited by the type of reagents or samples. For example, the reagents can be dry reagents or liquid reagents of any suitable chemical compositions. The samples can be human body fluids, animal body fluids, or non-body fluids.

The technology described in this document facilitates configuration of containers with shorter optical paths (e.g., 6 mm or less) without affecting the quality/reliability of measurements. Specifically, the concomitant reduction of the reaction volume in the reduced dimension containers can facilitate a more efficient mixing of sample and reagents that results in an assay where reduced fluidic noise (as compared to that seen in some existing containers) at least offsets any degradation of sensitivity due to the reduced optical path length. Specifically, although the amount of absorbance may be reduced due to the shorter optical path length, the overall SNR associated with the fluid testing can remain unchanged (or even improve) as compared to the SNR associated with longer optical path lengths t. The containers with shorter optical path lengths (e.g., 6 mm, 5.5 mm, 5 mm, 4 mm or less) can in turn facilitate smaller fluid volumes (e.g., 120 µL, 110 µL, 90 µL, or less) that require less sample volume, less reagent volume, or both, (e.g., 30%-50% reduction) as compared to that for containers with higher optical path lengths. Therefore, more testing can be performed from a given amount of reagent volume, and/or less sample may have to be drawn from a patient. In some implementations, the containers with reduced optical path lengths (and therefore reduced reaction volumes) can potentially speed up the process of testing by reducing dispensing/mixing time and therefore improving efficiency of the overall testing process.

Further, the technology described in this document provides an aspirate-dispense mixing process that uses a reduced blind volume (amount of sample left in the container upon aspiration) to improve the mixing efficacy. For example, if a dispenser/aspirator nozzle can be lowered into a container up to a certain height from the floor of the container, the amount of assay left in the container after aspiration (i.e., the blind volume) would be lower for a container with smaller internal dimensions. As such, the smaller the internal dimensions of a container, the lower the corresponding blind volume. Further, a lower blind volume implies that a larger percentage of the fluid can be aspirated and dispensed back into the container to facilitate better mixing of the reagents and samples. Such improved mixing can in turn reduce the fluidic noise and improve the quality and sensitivity of the fluid testing result.

FIG. 1 is a diagram of an example system 100 configured to implement technology described herein. The system 100 includes a container, e.g., a cuvette 101, that includes one or more container wells (e.g., container well 102a and container well 102b, 102 in general). In some configurations, a cuvette can include an array of several identical container wells (e.g., 4, 6, or 8 containers), or a single container well. Each container well 102 is configured to hold a fluid 106 that is to be tested by the system 100. The fluid can include aliquots of a reaction mixture, biological sample (e.g., blood plasma, whole blood, urine), or factions of samples thereof. For example, the fluid can include blood plasma sample, a reagent, or a mixture of the blood sample and the reagent, which is used to perform hemostasis diagnostic tests. The fluid in each container well can be tested independently of other fluids in other container wells. For simplicity, the descriptions of this disclosure use containers and container wells interchangeably, as the methods and systems described herein are not limited by whether or not a container has a single container well or multiple container wells.

Each container well 102 includes an upper portion 103 and a lower portion 104, and the upper portion has a wide opening for a probe 122 to aspirate or dispense fluid 106 (e.g., a biological sample and/or a reagent). The length 126 and width 128 of the lower portion 104 can be configured to be less than 6 mm each, e.g., between 3.3 mm to 5.5 mm. In some implementations, the length 126 and width 128 represent the interior dimensions of the lower portion 104. In some implementations, the length 126 and width 128 of the lower portion 104 can be 4 mm and 4.2 mm, respectively. In some implementations, the length 126 and the width 128 can be substantially equal to each other (e.g., 4 mm, 4.2 mm, or 5.34 mm). Compared with a conventional container or container well that has at least 6.67 mm in length and has a 150 µL in reaction volume, a container with 4 mm in optical path can have a 30%-50% lower reaction volume (i.e., 105 µL-75 µL)

The system 100 includes an optical source 108. For each container well, the optical source 108 can provide a light beam configured to traverse an optical path through the fluid in the container well. For example, the optical source 108 can provide a first light beam 114 (i.e., optical beam) from a first aperture 110 (e.g., a through hole) and a second light beam 111 from a second aperture 112. The size and the location of each aperture can determine the size of the light beam and the location of the light beam that passes through a respective container well 102. The optical path is a portion of the total path of the light beam delimited by the dimensions of the container well. For example, the length of the optical path through the fluid 106 can be determined by the length 126 of the lower portion 104 of the container well 102. Thus, when the length 126 of the lower portion of the container well 102 is between 3.3 mm to 5.5 mm, the length of the optical path through the fluid is between 3.3 mm to 5.5 mm. The light beam can include light of different colors (e.g., red, green, blue) or wavelengths that can be configured to measure different characteristics of the biological fluid.

Figure 3A:
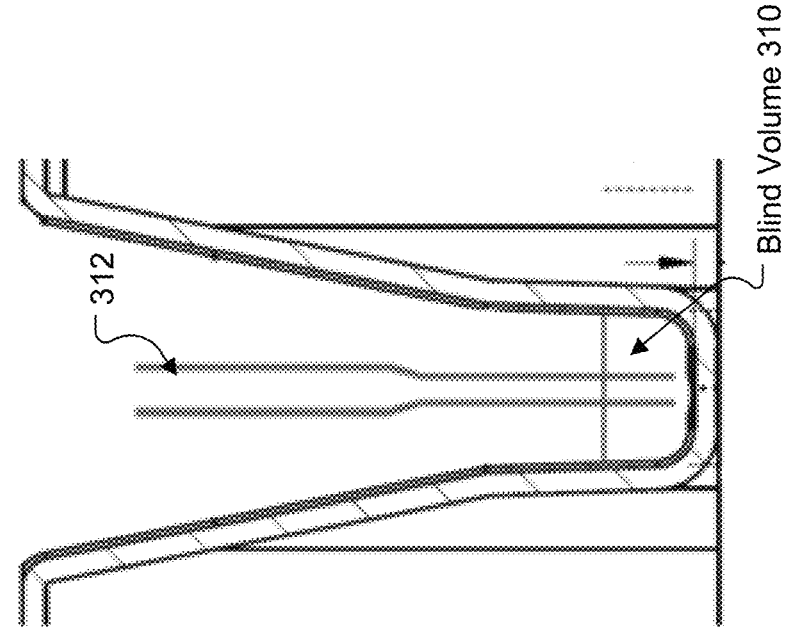
FIG. 3A is a schematic illustration of a light beam traversing through the fluid in the container.

The diameter of the light beam can be configured such that the diameter/width of the beam is less than the width 128 of the container well such that the entire beam traverses the optical path through the fluid. FIG. 3A shows an example of a light beam 306 traversing through the fluid in a container 304. In some implementations, the light beam 306 can be substantially identical to one of the light beams 111 or 114 of FIG. 1. In some implementations, the container 304 is substantially identical to the container wells 102 of FIG. 1. In some implementations, the container 304 can have a width of 4 mm and the beam size (e.g., diameter or width) can be within a range between 2.5 mm and 3.5 mm, as shown in the example of FIG. 3A. The light beam can be configured/positioned such that the top of the beam is sufficiently below the fluid surface 308. In some cases, this can be beneficial, for example, because fluidic noise (e.g., due to the meniscus effects at the fluid surface 308, splatter, uneven absorbance, insufficient mixing, or bubbles) dominates in a region near the fluid surface 308. To avoid such fluidic noise and to increase the accuracy of the measurements, the center of the light beam can be configured to be at a height that is less than a predetermined distance (e.g., 1.6 mm) from the bottom interior surface (or the floor) of the container. In the example of FIG. 3A, the center of the light beam 306 is at a height 302 of 1.4 mm from the bottom interior surface of the container 304.

Referring back to FIG. 1, the system 100 includes an optical detector (e.g., the detectors 118 and 120) configured to receive optical information 133 after the light beam traverses the optical path. The optical information 133 can indicate one or more characteristics of the biological sample included in the fluid 106. The optical detector is positioned on the opposite side of container well 102 to obtain an optical reading that represents one or more characteristics of the fluid. In some implementations, a mechanical mounting system can hold the optical source 108, the detector board 116 (or the detectors 118 and 120), and the cuvette 101 that includes the one or more container wells 102. For example, the system 100 includes a first optical detector 118 configured to receive optical information after the first light beam 114 traverses the fluid 106 in the first container well 102a. The system 100 includes a second optical detector 120 configured to receive optical information after the second light beam 111 traverses the fluid in the second container well 102b. The first optical detector 118 and the second optical detector 120 can be mounted to the same detector board 116 such that both detectors can be moved together.

The system 100 includes one or more probes (e.g., the probe 122). The probe can dispense the fluid or components of the fluid, e.g., reagents or samples, into the container. For example, the probe 122 can be a sample probe that dispenses a biological sample (e.g., a blood plasma sample) into the container well 102. As another example, the probe 122 can be a reagent probe that dispenses a reagent into the container well 102. In some implementations, the same probe can dispense both the biological sample and the reagent. In some implementations, the probe can operate in a non-contact dispense process in which the probe 122 does not touch the fluid 106 in the container well 102. In some implementations, the probe 122 can operate in a contact dispense process in which the probe 122 can touch the fluid 106 in the container well 102. The probe can additionally be used for mixing the sample and the reagent(s). For example, the probe 122 can be configured to aspirate a portion of the fluid (leaving behind only a blind volume of fluid in the container) and dispense the aspirated portion back in the container.

Figure 3B:
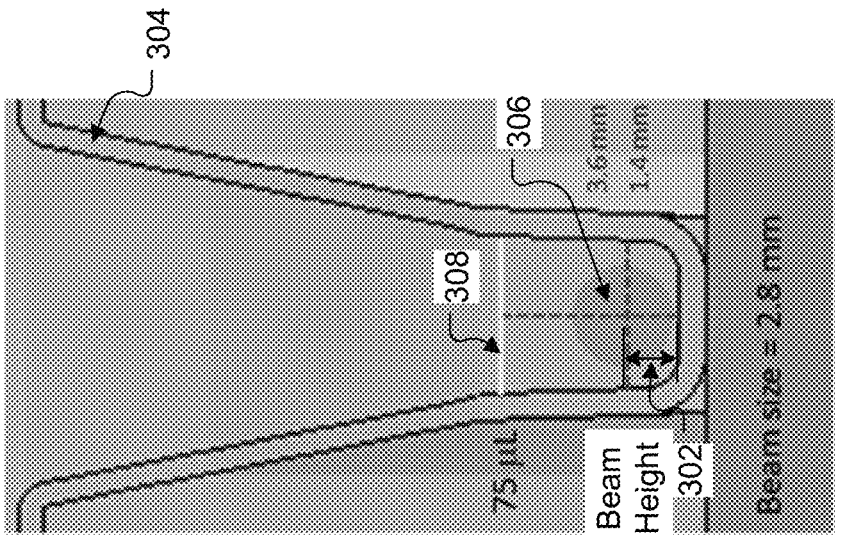
FIG. 3B shows a schematic illustration of an aspirate-dispense mixing process in the container.

FIG. 3B shows an example of an aspirate-dispense mixing process in the container. The probe 312 can be configured to aspirate a portion of the fluid in the container and dispense the aspirated portion of the fluid back into the container. In some implementations, as the probe aspirates, the probe continues to be lowered as the fluid surface is lowered due to aspiration. In some implementations, substantially all of the fluid can be aspirated and dispensed back in the container.

The volume of the fluid remaining in the container after aspiration can be referred to as the blind volume (BV) 310. In some implementations, to improve the mixing efficacy, the volume of the fluid remaining in the container after aspiration (BV) can be less than 40% or 35% or lower of the volume of the fluid in the container before the aspiration. Typically, the more fluid aspirated and dispensed during the aspirate-dispense mix, the lower the fluidic noise and the better the fluid quality. Thus, lowering the blind volume can improve the mixing efficacy and the homogeneity of the fluid, thereby reducing the fluidic noise and improving the fluid testing quality and SNR of the process. For example, referring back to FIG. 1, the volume of the fluid in the container well 102 before aspiration can be 75 μL, and the BV can be 25 μL, 20 μL, or 15 μL. Therefore, the BV can be 33%, 27% or 20% of the volume of the fluid in the container before the aspiration, resulting in improved mixing efficacy. In some implementations, the system can adjust the aspiration and/or dispensing speed to improve the mixing efficacy and the homogeneity of the fluid.

In some implementations, the volume of the fluid remaining in the container after the aspiration can be adjustable through a user input interface displayed on a displaying device (e.g., the monitor 130). For example, a user 132 can provide a value of the BV through an input device such as a keyboard 134 to a processing unit 124 that is connected to the system 100. In some implementations, the BV can be dependent on the type of fluid to be tested (e.g., assay dependent). In some implementations, the system can automatically determine the BV based on the type of test and/or the type of the fluid/assay in the container and the BV can be a customizable parameter for each assay. In some implementations, a user can determine an appropriate BV value based on the type of test and/or the type of the fluid/assay, and can provide the value of the BV through a user interface.

The system 100 can include a processing unit 124 that receives and/or processes the optical information 133. After receiving the light beam that traverses the optical path, the detector can generate the optical information 133 and can send the optical information 133 to the processing unit 124. The processing unit 124 can receive the optical information 133 and can process the optical information 133. The processing unit 124 can include one or more computers or servers of computers. The processing unit 124 can include hardware and/or software that are configured to analyze the optical information 133. The processing unit 124 can process the optical information 133 to generate values for at least one parameter (e.g., optical absorbance) of the biological sample. The processing unit 124 can perform evaluations related to the one or more characteristics of the biological sample using the at least one parameter. The processing unit 124 can display the at least one parameter and/or the evaluation result on a display (e.g., the monitor 130) for a user 132. In some implementations, the processing unit 124 can perform evaluations related to the one or more characteristics of the biological sample using the at least one parameter and one or more values (e.g., a threshold value). The one or more values can be hard-coded or can be adjustable through a user input interface. For example, a user 132 can determine an appropriate threshold value and can enter the value using a keyboard 134 connected to the processing unit 124. The processing unit 124 can be located at the same location as the rest of the system 100 (e.g., at the same location as the cuvette 101), or can be remote to the rest of the system 100 (e.g., on a cloud computing system).

In some implementations, the processing unit 124 can receive a user input for one or more parameters used in the fluid testing process through a user input interface (e.g., the keyboard 134 and the monitor 130). Examples of the one or more parameters used in the fluid testing process include assay-specific cuvette blind volume, probe dispense height, dispense speed, dispense volume during mixing, and other parameters for in the testing process. Thus, instead of using hard-coded parameters, the one or more parameters used in the fluid testing process can be flexibly adjusted by a user of the system 100.

FIG. 2 is a flowchart of an example process 200 for performing fluid testing in accordance with technology described herein. In some implementations, at least a portion of the process 200 may be executed by one or more components associated with the system 100 described with reference to FIG. 1. In some implementations, at least a portion of the process 200 may be executed at one or more servers (such as servers or computing devices in a distributed computing system), and/or one or more mobile devices (such as smartphones) in communication with the system 100 described with reference to FIG. 1.

Operations of the process 200 include dispensing a fluid including a biological sample and/or a reagent in a container, (202). The volume of the fluid to be dispensed is less than 120 μL. In some implementations, the volume of the fluid to be dispensed can be less than 100 μL, less than 75 μL, or less than 50 μL. In some implementations, the length and width of a portion of the container configured to contain the fluid can be less than 6 mm, e.g., between 3.3 mm to 5.5 mm and between 3.3 mm to 5.5 mm, respectively. In some implementations, the ratio of the length and width of the portion of the container configured to contain the fluid can be 1:1, e.g., the length can be substantially equal to the width. For example, the length and width of the portion of the container configured to contain the fluid can be 4 mm and 4 mm, respectively.

Operations of the process 200 also include providing, by an optical light source, a light beam configured to traverse an optical path through the fluid in the container, and a length of the optical path through the fluid is less than 6 mm, e.g., between 3.3 mm to 5.5 mm, or between 3.3 mm to 4.5 mm, and a center of the light beam is at a height less than 1.6 mm from a bottom interior surface of the container (204). The optical path is a portion of the total path of the light beam delimited by the dimensions of the container. In some implementations, the length of the optical path through the fluid can be 4 mm.

The location of the light beam can be adjusted such that the beam is at least a threshold distance below the fluid surface. For example, the location and/or size of the light source can be modified/adjusted such that the light beam from the light source passes through the fluid dispensed in the container. For example, referring to FIG. 1, the system can reduce the size of the window 110, such that the beam size (e.g., the diameter of the light beam) is reduced (e.g., the diameter of the beam equals a value that is within a range between 2.5 mm to 3.5 mm). The system can lower the position of the window such that the center of the light beam 114 is at a height less than 1.6 mm from the bottom interior surface of the container well 102. That is, the light beam can be lowered based on the reduced fluid fill height in the container.

In some implementations, operations of the process 200 can include aspirating, by a probe 122, a portion of the fluid in the container and dispensing, by the probe, the aspirated portion of the fluid back into the container. A volume of the fluid remaining in the container after aspiration can be less than 40% of the volume of the fluid in the container before the aspiration. In some implementations, the volume of the fluid remaining in the container after the aspiration can be adjustable through a user interface (e.g., through a keyboard 134 and a monitor 130 of a computer).

Referring back to FIG. 2, operations of the process 200 also include receiving, by an optical detector, optical information after the light beam traverses the optical path, wherein an output of the optical detector is associated with at least one parameter representing the one or more characteristics of the biological sample (206). In some implementations, the system can be configured to modify the location of a read head of the detector in accordance with the container described herein in which the volume of fluid contained is less than 120 μL. For example, referring to FIG. 1, compared to a conventional container where a volume of fluid to be contained is more than 120 μL, the system can lower the position of a read head of the detector 119 because the light beam 114 has been lowered. In some implementations, an area of the read head of the detector 119 on which the optical beam is collected (e.g., the collection aperture) can be adjusted. For example, the system can set the diameter of the collection aperture to a value that is within a range between 2.5 mm and 3.5 mm.

In some implementations, operations of the process 200 can include receiving, by a processing unit, the optical information, processing (208), by the processing unit, the optical information to generate values for the at least one parameter including optical absorbance, and performing (210), by the processing unit, evaluations related to the one or more characteristics of the biological sample using the at least one parameter and one or more values adjustable through a user input interface. The system can be configured to determine the one or more characteristics of the biological sample using the at least one parameter. For example, the at least one parameter can be optical absorbance of the light beam by the fluid measured by the detector, and the one or more characteristics of a blood sample during a hemostasis diagnostic test can include clotting factor assays, D-Dimer and other fibrinogen breakdown products, heparin and anti-Xa assays, fibrinogen assays, partial thromboplastin time, prothrombin time, and Factor XIII assay. The system can perform an evaluation related to the one or more characteristics of the biological sample using the at least one parameter (e.g., the optical absorbance, attenuation, or scattering) and one or more values (e.g., thresholds). For example, the system can be configured to determine that one or more parameters of the optical absorbance is within a reasonable range to make sure the testing result is valid (e.g., not invalid due to bubbles or other trapped liquid or clot in the fluid).

Figure 4:
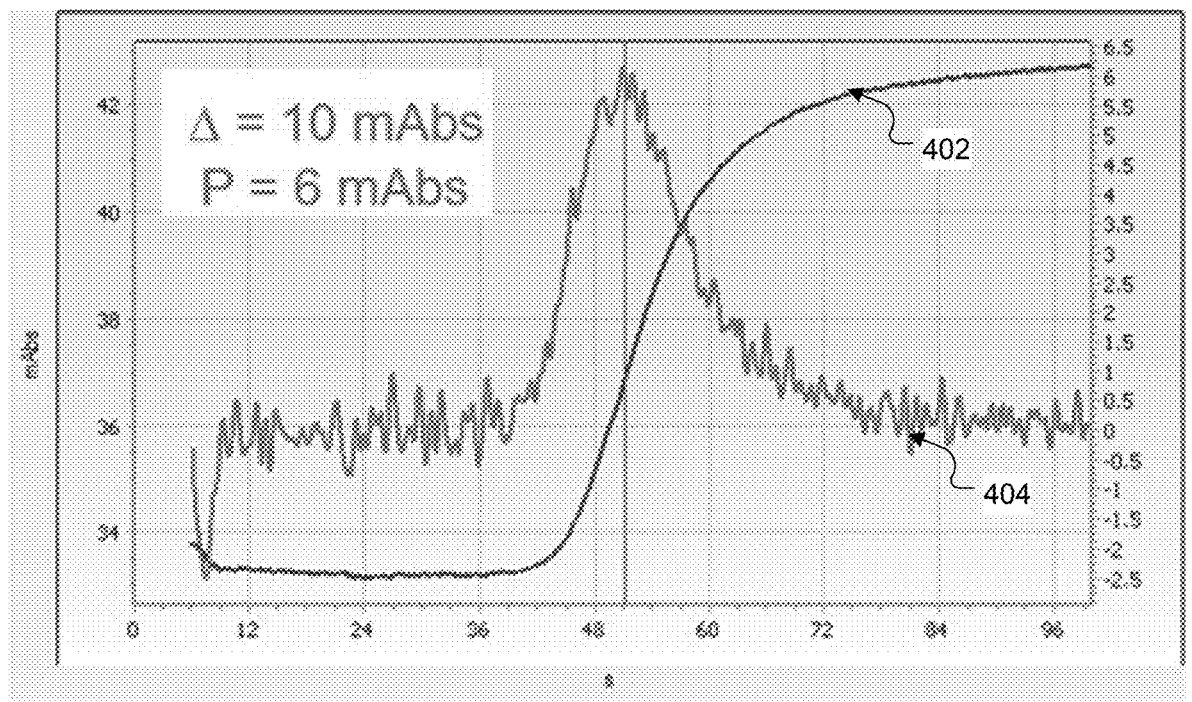
FIG. 4 shows an example of a plot illustrating path length sensitivity associated with a container in accordance with technology described herein.

FIG. 4 shows an example of a plot illustrating path length sensitivity. The system can be configured to compute a change in the absorbance corresponding to the fluid over a period of time. For example, the line 402 indicates the optical absorbance in milli-absorbance (mAbs) measured by the detector as a function of time (in seconds) as the blood sample clots. The unit mAbs represents normalized optical density as a ratio of (i) a measured intensity, to (ii) a reference intensity representing absorbance of a reference fluid (e.g., water or saline). The optical absorbance is roughly flat at the beginning, but quickly ramps up during the time period between 40 seconds and 60 seconds, and then rises at a slower speed after the time point at 60 seconds. Here, the change in absorbance over the period of time from 0 seconds to 100 seconds is about 10 mAbs. Although this change in absorbance is smaller than the change in absorbance in a testing system with a longer optical path length (e.g., 6 mm to 7 mm), the signal fidelity is similar or better than the signal in a testing system with a longer optical path length. In some implementations, the system configurations (e.g., dispense height and mixing profiles, etc.) can be optimized and reconfigured based on the shorter path length. As such a test conducted using a container as described herein (e.g., with 4 mm optical path length) can be at least as robust to fluidic noise as one conducted with a container with a longer optical path length (e.g., 6 mm to 7 mm). The system can also compute a derivative of the absorbance over the period of time. For example, the line 404 is the derivative of the line 402. The system can also be configured to determine a peak of the derivative. For example, the peak of the derivative, as determined from the line 404, is approximately at P=6 mAbs.

The system can be configured to perform an evaluation of the blood sample by comparing the change in absorbance (e.g., 10 mAbs) and the derivative of the absorbance (e.g., 6 mAbs) with corresponding thresholds. In response to the change in container size and dimensions, the thresholds used for the evaluation change accordingly. In some implementations, the thresholds are precalculated and programmed. The system can have one or more prefixed thresholds for use, or can automatically select from the precalculated thresholds based on the testing needs. In other implementations, the system can allow, e.g., prompt, a user to provide threshold inputs, improving the reliability of the measurement. In some cases, if the change in absorbance is less than a threshold, the corresponding measurement may be deemed as potentially unreliable. As such in some implementations, the process 200 can include performing a check whether the absorbance and/or the derivative thereof satisfy certain thresholds. For example, the system can be configured to determine whether the change in absorbance over a period of time is larger than or equal to a first threshold and/or a change in a derivative of the absorbance over a period of time is larger than or equal to a second threshold. In some cases, responsive to determining that the change of absorbance is larger than or equal to the first threshold and/or the peak of the derivative is larger than the second threshold, the system is configured to determine that the one or more characteristics determined by the system represents a valid result. Conversely, responsive to determining that the change of absorbance is lower than the first threshold or the peak of the derivative is lower than the second threshold, the one or more characteristics determined by the system can be determined as likely to be erroneous. The technology described herein can allow for lower thresholds without compromising the accuracy of the results. For example, referring to FIG. 4, the change in absorbance (as represented by the curve 402) over the period of time from 0 seconds to 100 seconds is about 10 mAbs and the peak of the derivative curve 404 is about 6 mAbs. In comparison, the corresponding thresholds for longer optical path lengths (e.g., a 6.67 mm optical path length) can be 18 mAbs and 14 mAbs, respectively, for similar assays. The lower thresholds used in connection with the technology described herein can be assay-specific and based on experimental/empirical data. In some implementations, the process 200 can include an option for a user to input the thresholds for a particular assay.

In some implementations, the system can be configured to modify the first threshold of change in absorbance to account for the impact of a shorter optical path length. For example, the system can obtain a first threshold (e.g., 8 mAbs)—potentially via user-input—that corresponds to a corresponding assay in a short optical path length. The system can determine that the change in absorbance (e.g., 10 mAbs) is larger than the first threshold (e.g., 8 mAbs), and determine the reliability of the measurements accordingly. The system can also determine whether the peak of the derivative is larger than or equal to a second threshold. For example, the system can be configured to obtain a second threshold (e.g., 5 mAbs)—potentially via user input—that corresponds to the particular assay and the short optical path length. The system can determine that the peak of the derivative (e.g., 6 mAbs) is larger than the second threshold (e.g., 5 mAbs), and determine the reliability of the measurements accordingly. For example, referring to FIG. 4, because the change of the absorbance is larger than 8 mAbs and the peak of the derivative is larger than 5 mAbs, the system can be configured to determine that the results of the underlying hemostasis diagnostic test represent likely valid results. If the system determines that the change of the absorbance is lower than the first threshold, and/or the peak of the derivative is lower than the second threshold, the system can be configured to flag the results as likely erroneous.

In some implementations, one or more values (e.g., the values for the first threshold and/or the second threshold explained above in reference to FIG. 4) can be adjustable. Rather than having a hard-coded value, the value can be adjusted by a user, e.g., through a user input interface. For example, a user can enter the values for the first threshold and the second threshold using a keyboard and a mouse through a user interface. In some implementations, the one or more values can be dependent on the type of the fluid (e.g., the biological sample and the reagent). The system can automatically determine the one or more values based on the type of the fluid/assay, or a user can adjust the one or more values based on the type of the fluid.

Other examples of thresholds that can be similarly pre-programmed or user controlled include linearity thresholds used to trigger secondary algorithms, and alternative dilutions used in D dimer, HIT, vWF and other latex turbido-metric immunoassays.

Referring back to FIG. 2, in some cases, the distance of the probe tip from the fluid surface (also referred to as dispense height) can affect the accuracy of the test. For example, dispensing from a height larger than a threshold from the liquid surface can cause bubble formations or other artifacts that may affect the readings. Compared with fluid testing with longer optical path lengths (e.g., 6 mm to 7 mm), the dispense heights for shorter optical path lengths (e.g., 3.5 mm to 5.5 mm) are typically different. In some implementations, the system can be configured to obtain the dispense height from a look-up table that is based on the dimensions of the container. The look-up table can be stored in a memory device associated with the system and the system can be configured to automatically perform optimization of the dispense height of the probe.

Figure 5:
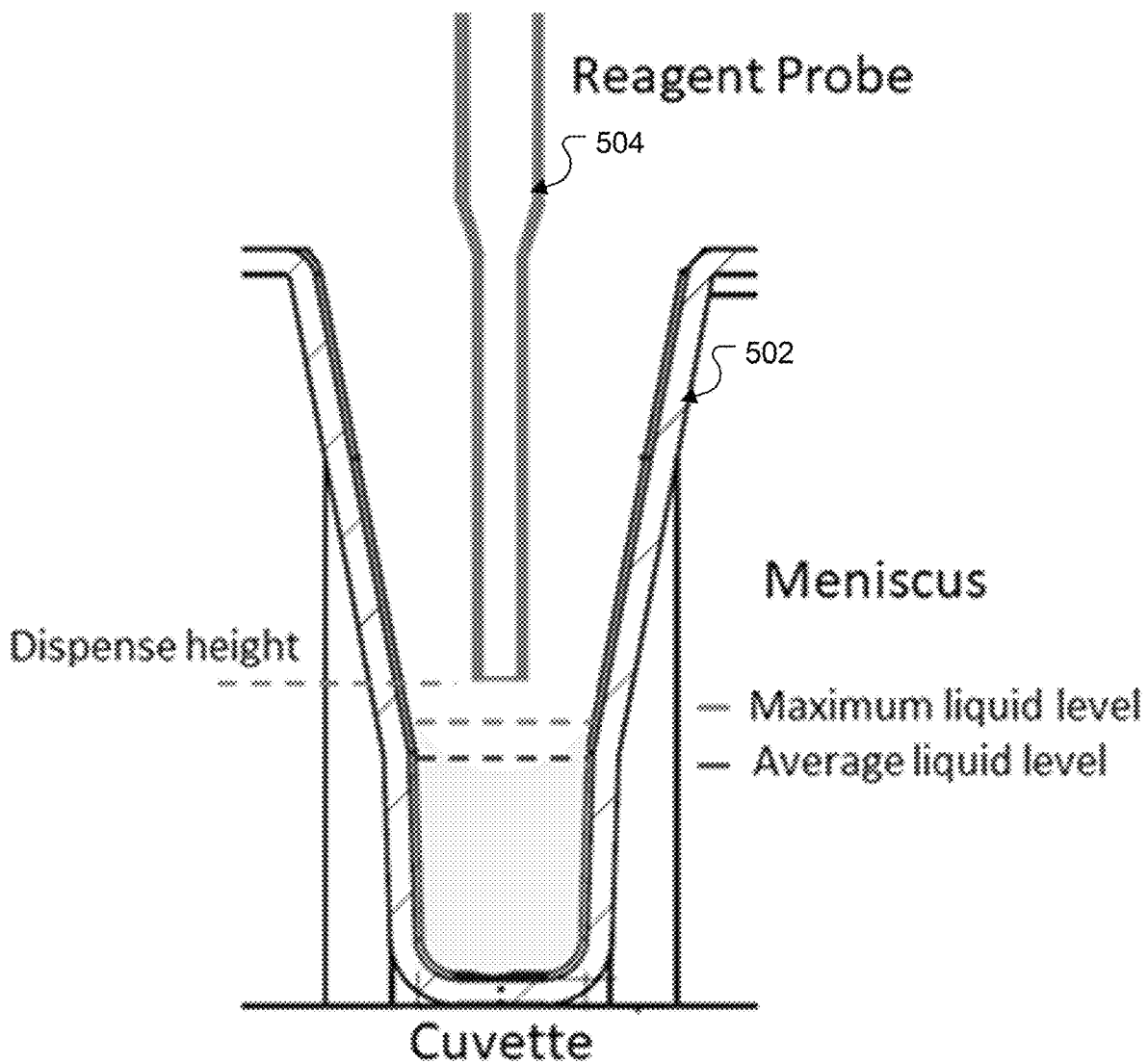
FIG. 5 is a schematic illustration of a dispensing mechanism into a container.

In some implementations, operations of the process 200 can include receiving, by a processing unit, information indicative of a composition of the fluid in one of the one or more containers, and determining, by the processing unit, based on the information indicative of the composition of the fluid, a dispense height of a corresponding probe above a surface of the fluid for dispensing at least one of the biological sample or a reagent component of the fluid. In some implementations, the determination of the dispense height of the corresponding probe can account for surface tension interactions between the fluid and walls of the container. For example, FIG. 5 shows a schematic illustration of a dispensing mechanism. This example illustrates that the system can be configured to perform an optimization of the dispense height of the probe 504 due to the different shape of the meniscus (i.e., liquid level not being flat across the container 502) of the container 502. The meniscus or the curve shape can be dependent on the cuvette geometry. Thus, the dispense height needs to be adjusted based on the different shape of the meniscus to avoid touching the liquid in the testing of certain assays. For example, it may be desirable for the probe 504 to be close enough to the liquid level to promote effective mixing, but not too close that it touches the liquid surface (e.g., in a non-contact dispense process). Surface tension due to interactions between the fluid and the walls of the container 502 can draw the fluid further up the walls of the container 502, especially in small containers (e.g., 3.5 mm to 5.5 mm path length containers), because the capillary forces can be inversely proportional to the width and/or length of the container 502. As such, the fluid in the container 502 can have a maximum liquid level that is slightly higher than the average liquid level of the surface (e.g., the expected flat liquid height without the meniscus). Thus, a higher dispense height (than what may be indicated by the average liquid level) may be desirable for some assays in the smaller dimension containers.

In some implementations, the dispense height can be between 2 mm and 4 mm from the average liquid level of the fluid in the container. For example, the system can determine the average liquid level based on the amount of fluid dispensed in the cuvette 502. The system can configure location of the reagent probe 504 such that the dispense height is between 2 mm and 4 mm from the average liquid level.

Various implementations of the systems and techniques described here can be realized in digital electronic circuitry, integrated circuitry, specially designed application specific integrated circuits (ASICs), computer hardware, firmware, software, and/or combinations thereof. These various implementations can include implementation in one or more computer programs that are executable and/or interpretable on a programmable system including at least one programmable processor, which may be for a special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural, object-oriented, assembly, and/or machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a cathode ray tube (CRT) or liquid crystal display (LCD) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a GUI or a web browser through which a user can interact with an implementation of the systems and techniques described here), or any combination of such back end, middleware, or front end components. The components of the system can be interconnected by any form or medium of digital data communication, such as network 210 of FIG. 2. Examples of communication networks include a LAN, a WAN, and the Internet.

The computing system can include clients and servers. A client and server are generally remote from each other and typically interact through a communication network. The relationship of client and server arises by virtue of computer programs running on the respective computers and having a client-server relationship to each other.

Although a few implementations have been described in detail above, other modifications may be made without departing from the scope of the inventive concepts described herein, and, accordingly, other implementations are within the scope of the following claims.

What is claimed is:

1. A system for determining one or more characteristics of a biological sample, the system comprising:

a cuvette configured to contain a fluid comprising the biological sample, where a volume of the fluid to be contained is less than 120 μL, wherein the cuvette comprises at least one pair of opposing surfaces that are substantially parallel to each other, the at least one pair of opposing surfaces defining a portion of the cuvette into which the fluid is dispensed or from which the fluid is aspirated, wherein a length of a portion of the cuvette configured to contain the fluid is between 3.3 mm to 5.5 mm and a width of the portion is between 3.3 mm to 5.5 mm;

a probe configured to dispense the fluid into the cuvette or aspirate a portion of the fluid from the cuvette;

an optical source external to the cuvette and the probe, the optical source disposed to provide a light beam through the cuvette, the light beam configured to traverse an optical path through the fluid in the cuvette along a direction substantially perpendicular to the at least one pair of opposing surfaces, the optical source being positioned external to the cuvette such that a center of the light beam is at a height less than 1.6 mm from a bottom interior surface of the cuvette; and an optical detector configured to receive optical information after the light beam traverses the optical path, wherein an output of the optical detector is associated with at least one parameter representing the one or more characteristics of the biological sample.

2. The system of claim 1, wherein a volume of the fluid remaining in the cuvette after aspiration is less than 35%, or less than 40% of the volume of the fluid in the cuvette before the aspiration.

3. The system of claim 2, wherein the probe is configurable through a user input interface, such that the volume of the fluid remaining in the cuvette after an aspiration by the probe is adjustable.

4. The system of claim 1, wherein the volume of the fluid to be contained is less than 100 μL, less than 75 μL, or less than 50 μL.

5. The system of claim 1, wherein a length of the optical path through the fluid is 4 mm.

6. The system of claim 1, comprising a programmable processor configured to:

receive and/or process the optical information to generate values for the at least one parameter including optical absorbance, and perform evaluations related to the one or more characteristics of the biological sample using the at least one parameter and one or more values adjustable through a user input interface.

7. The system of claim 1, comprising a programmable processor configured to:

receive information indicative of a composition of the fluid in the cuvette, and determine, based on the information indicative of the composition of the fluid, a dispense height of a corresponding probe above a surface of the fluid for dispensing at least one of the biological sample or a reagent component of the fluid, wherein the dispense height of the corresponding probe is determined by accounting for surface tension interactions between the fluid and walls of the cuvette.

8. The system of claim 7, wherein the dispense height is between 2 mm and 4 mm from an average liquid level of the fluid in the cuvette.

* * * * *